United States Patent [19]
Whiteman et al.

[11] Patent Number: 5,830,170
[45] Date of Patent: Nov. 3, 1998

[54] MULTIPLE-USE BLOOD-BLOTTING DEVICE

[76] Inventors: Phillip L. Whiteman; James D. Greene, both of 423 N. Palm Dr., #103, Beverly Hills, Calif. 90210

[21] Appl. No.: 820,127

[22] Filed: Mar. 19, 1997

Related U.S. Application Data

[60] Provisional application No. 60/014,088 Mar. 26, 1996.
[51] Int. Cl.$^6$ .......................... A61M 35/00; B65D 83/10
[52] U.S. Cl. ................................. 604/1; 206/362
[58] Field of Search ................... 604/1–3; 206/361–363, 206/440, 812

[56] References Cited

U.S. PATENT DOCUMENTS

| | | |
|---|---|---|
| 2,292,995 | 8/1942 | Greenwoll . |
| 2,431,203 | 11/1947 | Sebastian . |
| 2,727,515 | 12/1955 | Hoff . |
| 2,864,362 | 12/1958 | Hermanson et al. . |
| 3,162,306 | 12/1964 | Zackheim ................. 206/440 |
| 3,613,685 | 10/1971 | Reynolds . |
| 3,759,375 | 9/1973 | Nappi ....................... 206/362 |
| 3,826,259 | 7/1974 | Bailey . |
| 3,899,080 | 8/1975 | Brunda ..................... 206/531 |
| 3,976,195 | 8/1976 | Cohen ...................... 206/362 |
| 4,190,153 | 2/1980 | Olsen ....................... 206/362 |
| 4,317,852 | 3/1982 | Ogden . |
| 4,357,192 | 11/1982 | Moser . |
| 4,360,021 | 11/1982 | Stima . |
| 4,705,514 | 11/1987 | Barnard . |
| 4,799,488 | 1/1989 | Mintz . |
| 4,824,702 | 4/1989 | Straub . |
| 4,860,736 | 8/1989 | Kaitz et al. . |
| 4,989,733 | 2/1991 | Patry ........................ 206/440 |
| 5,182,191 | 1/1993 | Fan et al. . |
| 5,325,864 | 7/1994 | Gerber . |
| 5,328,450 | 7/1994 | Smith et al. . |
| 5,402,798 | 4/1995 | Swierczek . |

*Primary Examiner*—John G. Weiss
*Assistant Examiner*—Dennis Ruhl
*Attorney, Agent, or Firm*—Oppenheimer Wolff & Donnelly LLP

[57] ABSTRACT

A multiple-use blood-blotting device includes a sheet of base stock which has a plurality of fingertip-sized recesses formed therein. A corresponding plurality of absorbent swabs are received in the recesses. The swabs may be releasably attached to the recesses so that soiled swabs may be removed. Lines of perforations may be formed in the sheet of base stock, allowing the sheet of base stock to be divisible into sections, with each section including at least one recess and swab. A protective sheet may be attached to the sheet of base stock to cover and protect the swabs. The protective sheet may have perforations which corresponding to perforations in the sheet of base stock, so that each of the swabs remains sterile and hygienic even if device is divided into smaller sections.

17 Claims, 2 Drawing Sheets

MULTIPLE-USE BLOOD-BLOTTING DEVICE

CROSS REFERENCE TO RELATED APPLICATION

The present application claims priority under 35 U.S. §120 on United States Provisional Patent Application No. 60/014,088 filed Mar. 26, 1996.

FIELD OF THE INVENTION

The present invention relates to a medical device for clotting or blotting blood and, more particularly, to a medical device having a plurality of swabs for blotting blood on fingertips.

BACKGROUND OF THE INVENTION

Diabetes afflicts millions of people around the world. In the United States alone, there are more than 17 million insulin-dependent diabetics today. This number is expected to increase dramatically as the population grows older and lives longer.

Diabetics are divided into two types: Type I and Type II. The difference between the two types is in the amount of glucose levels in the blood, with Type I diabetics having much higher glucose levels than Type II diabetics. Accordingly, while Type I diabetics need to inject themselves with insulin on a daily basis, Type II diabetics only need to take oral medication.

In treating themselves, diabetics check their blood glucose level daily. In 1991, the American Medical Association endorsed a study which underscored the advantages of tight control for both types of diabetics. Type I diabetics were accordingly instructed to inject themselves with insulin three times per day and to test their blood glucose levels five times per day. Type II diabetics were instructed to test their blood glucose levels twice a day. In more extreme cases where glucose levels fluctuate wildly, the blood may need to be tested every half hour for a few hours on end.

As known, an insulin injection entails puncturing the skin with a needle, and a blood test entails pricking the tip of a finger. However minimal these procedures may be, they are both invasive and result in bleeding, particularly the blood test. Accordingly, a diabetic needs to swab or blot the injection or test sight for hygiene. Herein lies substantial inconvenience to the diabetic: after each blood test, a tissue, swab, or other absorbent material must be carried or be made available for each blood test.

When testing blood, kits are often used which contain all the equipment necessary for measuring glucose levels. Care must be taken not to soil the sensitive equipment. Accordingly, after pricking the end of a finger and applying the resultant blood drop to recording equipment, the user then needs to obtain a tissue or tear a paper towel off a roll to blot the finger. This may disrupt the test kit and, in any case, is inconvenient. Many diabetics tear little pieces off of paper towel to blot their fingers, which ends up being wasteful and messy.

Accordingly, there is a need for a medical device which may be used conveniently and hygienically to swab or blot an injection or blood-test site.

SUMMARY OF THE INVENTION

The present invention provides a multiple-use blood-blotting device which has a plurality of absorbent swabs which may be individually used to blot blood from a fingertip. The multiple-use blood-blotting device is convenient to use and is hygienic.

According to one aspect of the present invention, a multiple-use blood-blotting device includes a sheet of base stock which has a plurality of fingertip-sized recesses formed therein. A corresponding plurality of absorbent swabs are received in the recesses. A user may then, after pricking the end of a finger for a blood test, place the fingertip against one of the swabs to blot the blood.

Another aspect of the present invention is that the swabs may be releasably attached to the recesses. After a user blots blood in one of the swabs, the swab is soiled and may be removed from the device and discarded. This increases the hygienic nature of the device of the present invention.

According to yet another aspect of the present invention, lines of perforations may be formed in the sheet of base stock. This allows the sheet of base stock to be divisible into sections, with each section including at least one recess and swab. Preferably, the multiple-use blood-blotting device is configured as an array of swabs to allow a user to tear of sections of the device along the lines of perforations for use away from home or for daily use.

Another aspect of the present invention lies in the provision of a protective sheet which covers and protects the swabs. The protective sheet may be cellophane, for example. The protective sheet may have perforations which corresponding to perforations in the sheet of base stock, so that each of the swabs remains sterile and hygienic even if device is divided into smaller sections.

The multiple-use blood-blotting device according to the present invention may be inexpensively made. For example, the recesses may be made in the sheet of base material by a process known as debossing, which entails pressing the sheet of base material in a press to form the recesses. The swabs may then be readily applied within the recesses, with the protective sheet attached thereafter.

Other aspects, advantages, and features of the present invention will become apparent to those skilled in the art from the following detailed description of exemplary embodiments of the invention and accompanying drawings.

DETAILED DESCRIPTION OF EXEMPLARY EMBODIMENTS

Figure 1:
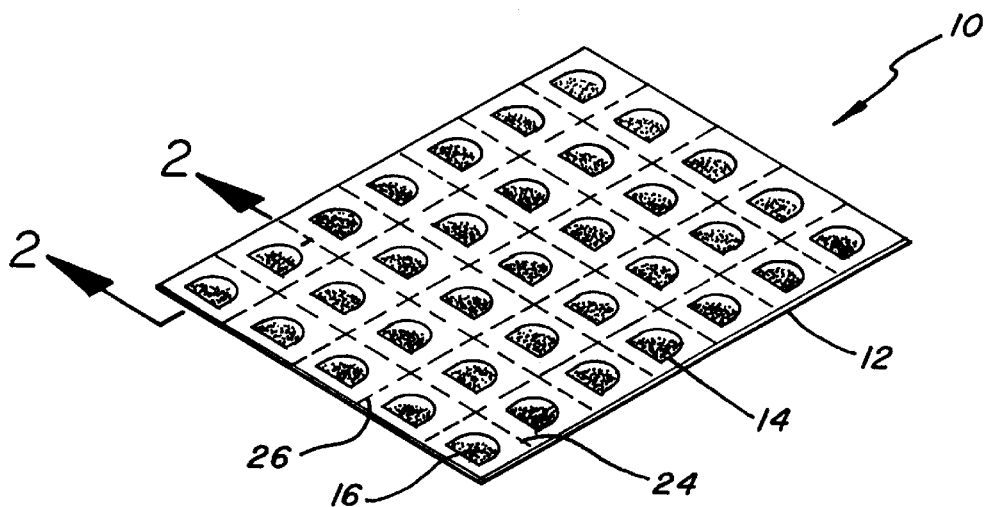
FIG. 1 is a perspective view of a multiple-use blood-blotting device shown in an exemplary embodiment in accordance with the present invention.

A multiple-use blood blotter 10 according to an exemplary embodiment of the present invention as illustrated in FIG. 1 provides a convenient and hygienic medical device for blotting blood. Many ailments such as diabetes require a patient to inject drugs or to draw blood every day or several times a day. This often involves pricking the tip of a finger to take a blood sample to measure, for example, blood glucose levels. The patient must then blot the tip of the finger to stop the bleeding.

The multiple-use blood blotter 10 includes base stock 12 with a plurality of fingertip-sized recesses 14 formed therein. Each of the recesses 14 is provided with a swab 16 made from an absorbent material. Each of the swabs 16 is releasably mounted in one of the recesses 14 so that the swab 16 may be removed from the recess 14.

When a user of the multiple-use blood blotter 10 has pricked a fingertip to test blood glucose levels, for example, the user may stop the resulting bleeding either by removing one of the swabs 16 and pressing the swab 16 against the fingertip or by pressing the fingertip against the swab 16 while the swab 16 is still received in the recess 14. In either case, as the swab 16 is removable from the blood blotter 10, the swab 16 may be sanitarily discarded after use.

Figure 2:
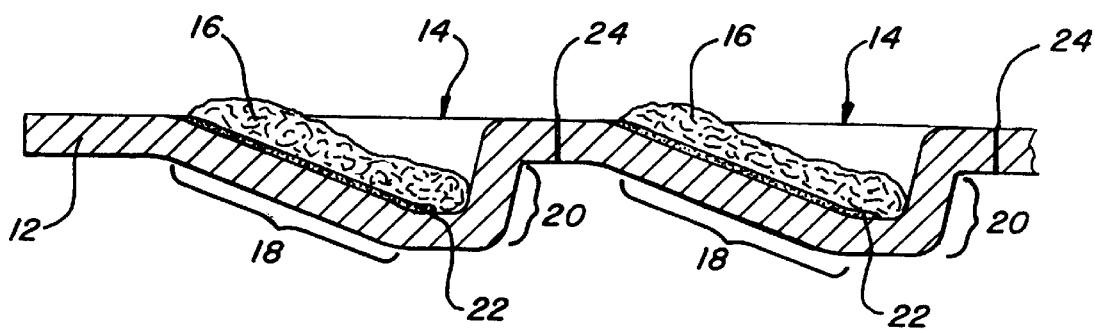
FIG. 2 is a cross-sectional view of a multiple-use blood blotter view taken along line 2—2 of FIG. 1, particularly showing the configurations of recesses in which swabs are received.

With additional reference to FIG. 2, the base stock 12 is preferably made from a readily available and easily workable material such as pressed paperboard or substantially rigid card stock. Accordingly, the recesses 14 may be easily and inexpensively formed in the base stock 12 by various processes but are preferably formed by a process known as "debossing," as opposed to embossing. During a debossing process, the base stock 12 may be placed on a mold and pressed by a corresponding mold to "punch" or "press" indentations through the base stock 12 to form the recesses 14. As particularly shown in FIG. 2, each of the recesses 14 may taper or slope from one end to the other, analogous to a swimming pool, which will be discussed in more detail below. The base stock 12 is preferable sized so that the blood blotter 10 is readily mobile and conveniently carried by a user for use at remote locations.

There may be any number of recesses 14 formed in the base stock 12 but the number should be adequate so as to be convenient and economical to users who need to test their blood several times a day. For example, there may be 35 of the recesses 14 formed in a seven-by-five array on the base stock 12. The recesses 14 and, correspondingly, the swabs 16 are preferably in the shape of a semicircle, which shape conforms to the shape of a fingertip. Therefore, the swabs 16 may be sized and shaped so that economical and efficient use may be made of the material comprising each of the swabs 16 in blotting blood on a fingertip.

Figure 3:
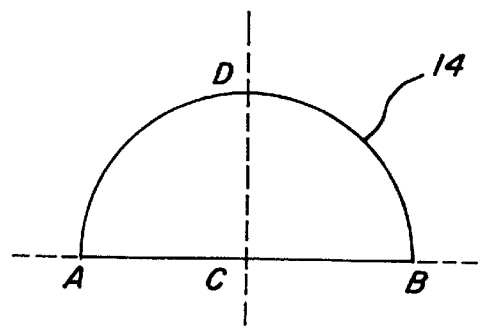
FIG. 3 is a schematic view of one of the recesses illustrated in FIG. 2.

With additional reference to FIG. 3, the recesses 14 are preferably formed to slope from diameter AB of the semicircle, down along axis CD of the semicircle, to a central apogee or arch-point D of the semicircle, thereby forming a slope portion 18 and a wall portion 20. When a user places a fingertip on a swab received in one of the recesses 12, the end of the fingertip may be positioned in the portion of the recess 14 which has a greater depth, that is, near the wall portion 20. Accordingly, a user may use the sense of touch to determine the optimal position in the recess 14 for the fingertip, with the fingernail abutting the wall portion 20.

The swabs 16, as mentioned above, conform to the shape of the recesses 12 and are preferably semicircular shaped. The swabs 16 may be either substantially uniform in thickness or tapered in thickness to correspond to the tapering of the recesses 14. In order for the swabs 16 to be releasably received in the recesses 14, a layer of pressure-sensitive adhesive 22 is provided between each of the swabs 16 and the recess 14 corresponding thereto. The pressure-sensitive adhesive 22 is preferably applied to the sloping portion 18 of the recess 14 prior to mounting the swab 16 in the recess 14. Alternatively, each of the swabs 16 may have the adhesive applied directly thereto.

The swabs 16 are made from an absorbent material which also preferably has antibacterial and/or germicidal qualities. For example, the swabs 16 may be impregnated with alcohol or other disinfectant. The swabs 16 may also contain a moisturizer. The swabs 16 may be die cut from large swaths of absorbent material or formed according to other methods known in the art. The adhesion factor of the pressure-sensitive adhesive 22 is preferably substantially low so that the swabs 16 are easily removable.

With further reference to FIG. 1, the base stock 12 preferably has horizontal perforations 24 and vertical perforations 26, thereby dividing the blood blotter 10 into rows and columns of swabs 16. Therefore, rather than having the swabs 16 releasably mounted in the recesses 14, a user may remove a used swab 16 or a row of swabs 16 by tearing the base stock along the horizontal and vertical perforations 24 and 26. Further, rather than carry the entire blood blotter 10 on person, a user may divide the blood blotter 10 into smaller individual sections, for example, one or two rows or columns of swabs 16 which may be carried in a shirt pocket, for short-term use at a remote site. Further, large sheets of the blood blotter 10 may be economically fabricated and then divided into small sections by a manufacturer for individual sale or by a medical facility or an end user for individual use.

A preferred commercial embodiment of the multiple-use blood blotter 10 may be fabricated according to the following specifications. The base stock 12 is a sheet of Clear Cote card stock with dimensions of about 4¾ inches by 3½ inches and a thickness of about 1/32 inch. The recesses are 3/16-inch diameter semicircles and are arranged in seven rows and five columns. Vertical and horizontal spacing between each of the semicircular recesses 14 is about 2/16 inch. The depth of the recesses 14 is 3/16 inch at or near the wall portion 20. The swabs 16 are preferably less than about 3/16 inch in thickness. As those skilled in the art can appreciate, the size of the recesses 14 depends on the size of the fingers (including the little finger through the thumb which are all different sizes) of the end user. Accordingly, the recesses 14 may be configured in any dimension so as to fit the needs of the user.

The blood blotter 10 may be fabricated for commercial use according to alternative processes and specifications too numerous to elaborate on herein. However, a modification may be rather than forming the base stock 12 from card stock, the base stock 12 may be made from a plastic material which is easily molded to form the recesses 14. Accordingly, the base stock 12 is then reusable with a user replacing soiled swabs 16 with new swabs 16 having a pressure-sensitive-adhesive backing into the recesses 14. Also, the base stock 12 may have a fold line so that the blood blotter 10 may be folded in half along the fold line, thereby protecting the swabs 16 from contamination while carrying the blood blotter 10 in a pocket, purse, or the like. It may be desirable for manufacturers of blood-testing kits to include the multiple-use blood-blotting device 10 in their kits for customer convenience.

Figure 4:
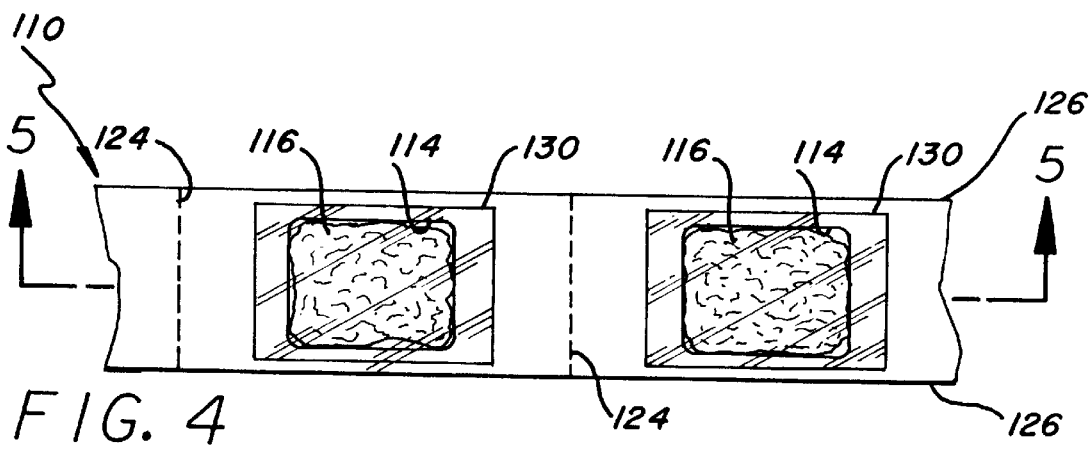
FIG. 4 is a plan view of another exemplary embodiment of the multiple-use blood-blotting device of the present invention.
Figure 5:
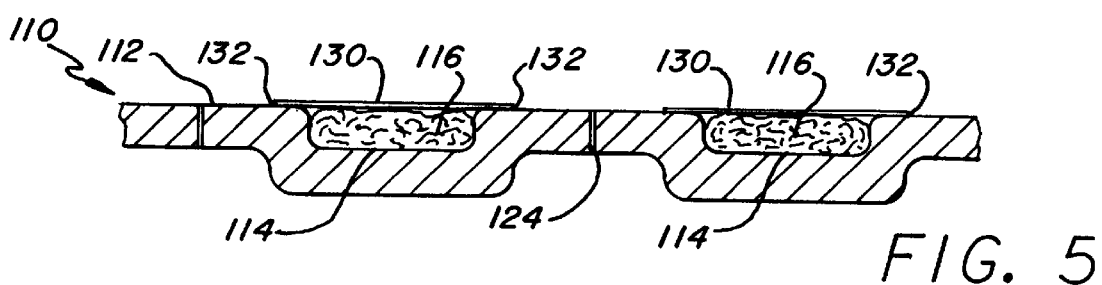
FIG. 5 is a cross-sectional view taken along line 5—5 of FIG. 4.

With reference to FIGS. 4 and 5, an alternative embodiment of the multiple-use blood-blotting device according to the present invention is shown. Reference numerals in FIGS. 4 and 5 are the same as those in FIGS. 1–3 when indicating analogous elements with the addition of a "1" as a prefix. For example, the recess 14 shown in FIG. 1 is indicated as recess 114 in FIGS. 4 and 5.

In this exemplary embodiment, the recesses 114 and the corresponding swabs 116 of the multiple-use blood-blotting device 110 are configured rectangularly to illustrate one of the many modifications and alternatives of the present invention. The multiple-use blood-blotting device 110 may also include a plurality of protective sheets 130, each corresponding to one of the recess/swab configurations. The protective sheets 130 may be made from any substantially hygienic material. For example, cellophane or other plastic sheet material may be used. It is preferable for clear sheet material to be used. The protective sheets 130 are preferably sized and configured so as to fit within the area defined by the horizontal and vertical perforations 124 and 126.

The protective sheets 130 are preferably removably attached to the base stock 112. This may be accomplished by a strip or dab of pressure-sensitive adhesive 132 placed between each of the protective sheets 130 and the base stock 112. Alternatively, the protective sheets 130 may be "spot welded" to the base stock 112, so to speak, by melting the protective sheets 130 and thereby adhering the sheets to the base stock 112 (if the protective sheets 130 are made from plastic material in a particular commercial embodiment). Also, permanent adhesive may be used. However, attaching the protective sheets 130 by pressure-sensitive adhesive 132 is preferable because after the swab 116 has been soiled with blood, the protective sheet may be replaced over the recess and soiled swab, thereby increasing the hygienic nature of the present invention. The pressure-sensitive adhesive 132 (or spot welding) may be configured around the entire perimeter of each protective sheet 130 or may be at intermittent locations, for example, one or two small dabs or strips for each side of the protective sheet.

Figure 6:
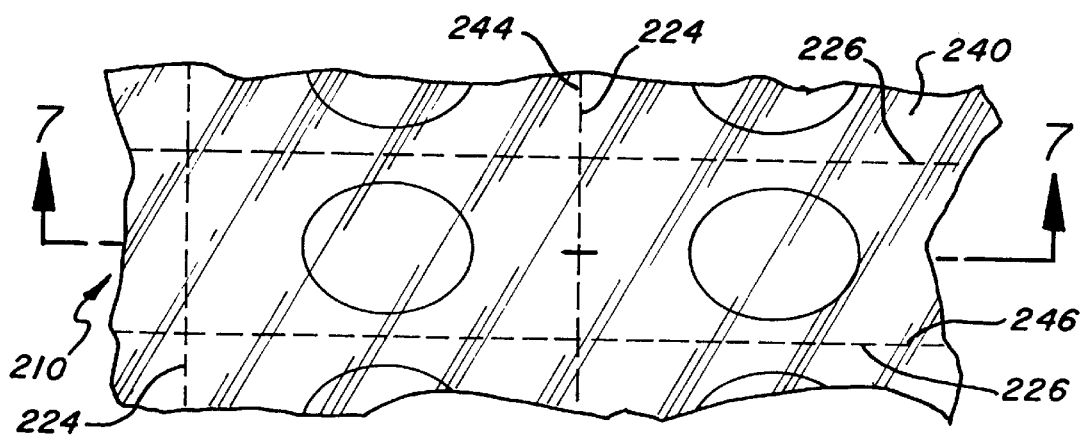
FIG. 6 is a plan view of yet another exemplary embodiment of the multiple-use blood-blotting device of the present invention.
Figure 7:
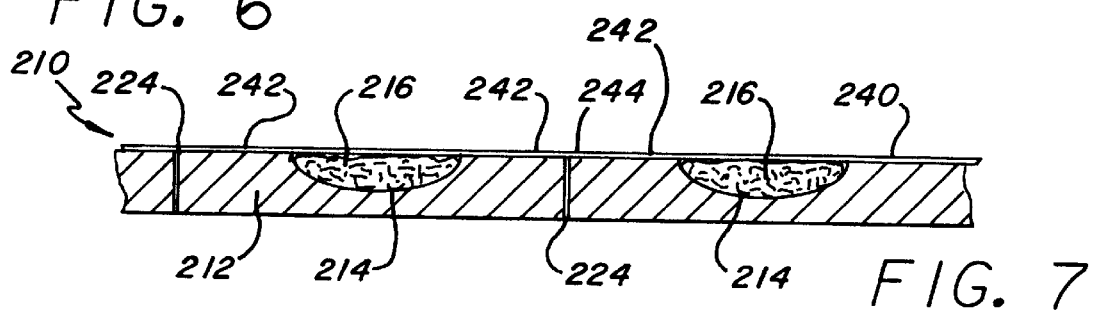
FIG. 7 is a cross-sectional view taken along line 7—7 of FIG. 6.

The multiple-use blood-blotting device of the present invention is further exemplified by the embodiment illustrated in FIGS. 6 and 7. Maintaining the same numbering convention as outline above, reference numerals in FIGS. 6 and 7 are the same as those in FIGS. 1–3 when indicating analogous elements with the addition of a "2" as a prefix.

In this embodiment, the recesses 214 and the swabs 216 of the device 210 are configured circularly. Also, rather than debossing the base stock 212 to form the recesses 214, the recesses 214 are configured as depressions in the base stock 212 itself. Accordingly, the back of the base stock 212 is substantially smooth.

The multiple-use blotting device 210 illustrated in FIGS. 6 and 7 includes a protective sheet 240 which substantially covers the entire base stock 212. The protective sheet 240 is attached to the base stock 212 in each of the divisions defined by the perforations 224 and 226, which is indicated by reference numeral 242. The attachment may be accomplished in a manner analogous to that described above in relation to the protective sheets 130 of FIGS. 4 and 5.

The protective sheet 240 has horizontal perforations 244 and vertical perforations 246 which correspond to the perforations 224 and 226 of the base stock 212. Accordingly, if a user divides the base stock 212 along perforations 224 and 226, the protective sheet 240 will also divide along perforations 244 and 246.

Those skilled in the art will further appreciate that the present invention may be embodied in other specific forms without departing from the spirit or principles of the invention, and although the present invention discloses only exemplary embodiments thereof, it is to be understood that other variations are contemplated as being within the scope of the present invention. For example, the base stock may not have any recesses formed therein, with the swabs being adhered directly to the face of the base stock. In addition, the exemplary embodiment shown in FIG. 1 may also be provided with a protective sheet as described in relation to FIGS. 4 and 6. Accordingly, the present invention is not limited to the particular embodiments which have been described in detail herein but is defined by the appended claims.

What is claimed is:

1. A multiple-use blood-blotting device for blotting a fingertip after being pricked for a blood sample, the device comprising:

a sheet of base stock divided into a plurality of sections by lines of perforations;

a plurality of fingertip-sized recesses formed in the sheet of base stock; and a plurality of absorbent swabs releasably attached in the plurality of recesses, by pressure-sensitive adhesive each of the swabs for absorbing blood;

each of the sections including at least one recess and swab.

2. The device of claim 1 further comprising a plurality of protective sheets respectively covering the plurality of swabs;

each of the protective sheets being removably attached to the sheet of base stock.

3. The device of claim 1 further comprising a protective sheet covering the plurality of swabs;

the protective sheet having perforations corresponding to the perforations of the sheet of base stock;

the protective sheet being attached to the sheet of base stock at a plurality of locations corresponding to the plurality of recesses.

4. The device of claim 1 wherein the recesses are formed by debossing the sheet of base stock.

5. The device of claim 1 wherein the recesses are tapered in depth from one end to another.

6. The device of claim 5 wherein each of the recesses is formed as a semicircle with a diameter and a central apogee;

the recesses sloping downward from the diameter of the semicircle to the central apogee to form a slope portion and a wall portion.

7. The device of claim 1 wherein each of the swabs contains a moisturizer.

8. A method of making a multiple-use blood-blotting device comprising the steps of:

providing a sheet of base stock;

forming perforations in the sheet of base stock;

forming a plurality of fingertip-sized recesses in the sheet of base stock; and releasably attaching an absorbent swab by pressure-sensitive adhesive in each of the recesses for absorbing blood.

9. The method of claim 8 further comprising the step of:

attaching a protective sheet to the sheet of base stock to cover the swabs.

10. The method of claim 9 further comprising the step of: forming perforations in the protective sheet.

11. The method of claim 8 wherein said forming step includes the step of:

forming a plurality of tapering semicircular recesses in the sheet of base stock.

12. A multiple-use blood-blotting device comprising:

a sheet of base stock divided into a plurality of sections by lines of perforations; and a plurality of absorbent swabs releasably attached to the sheet of base stock by pressure-sensitive adhesive, each of the swabs for absorbing blood;

each of the sections of the sheet of base stock having at least one swab attached thereto.

13. The device of claim 12 wherein the sheet of base stock has a plurality of recesses formed therein;

each of the swabs being releasably attached in one of the recesses.

14. The device of claim 13 further comprising a protective sheet attached to the sheet of base stock to cover the swabs;

the protective sheet having lines of perforations which correspond to the lines of perforations of the sheet of base stock.

15. A multiple-use blood-blotting device comprising:

a sheet of base stock divided into a plurality of sections by lines of perforations; and a plurality of fingertip-sized recesses formed in the sheet of base stock; and a plurality of absorbent swabs releasably attached in the plurality of recesses by pressure-sensitive adhesive.

16. A method of making a multiple-use blood-blotting device comprising the steps of:

providing a sheet of base stock;

forming a plurality of recesses in the sheet of base stock;

releasably attaching an absorbent swab in each of the recesses with pressure-sensitive adhesive; and forming perforations in the sheet of base stock.

17. A multiple-use blood-blotting device comprising:

a sheet of base stock divided into a plurality of sections by lines of perforations, each of the sections having at least one recess formed therein; and a plurality of absorbent swabs, each of the swabs being releasably attached in one of recesses by pressure-sensitive adhesive.

* * * * *